United States Patent [19]

Georgusis

[11] Patent Number: Plant 6,964

[45] Date of Patent: Aug. 1, 1989

[54] SPATHIPHYLLUM CULTIVAR 'GORGUSIS NO. 1'

[75] Inventor: James J. Georgusis, Hollywood, Fla.

[73] Assignee: Oglesby Plant Laboratories, Inc., Altha, Fla.

[21] Appl. No.: 239,819

[22] Filed: Sep. 2, 1988

[51] Int. Cl.[4] ..... A01H 5/00

[52] U.S. Cl. ..... Plt./88

[58] Field of Search ..... Plt./88

*Primary Examiner*—James R. Feyrer
*Attorney, Agent, or Firm*—Frank B. Robb

[57] ABSTRACT

A Spathiphyllum cultivar of taller, wider habit with few suckers, longer, broader and darker, more shiny leaves, and white flowers.

1 Drawing Sheet

This invention relates to a new and distinct Spathiphyllum cultivar, which has been developed to meet certain conditions, primarily darker color and taller wider habit than prior known varieties with the leaf color darker and the leaves more shiny, than either of its parents.

In an environment where it is suitable to develop plants of this kind and particularly where they may be asexually reproduced by tissue culture, the instant cultivar is and has been so reproduced.

I have chosen to identify the Spathiphyllum hereof for record purposes as Georgusis No. 1 and it will be known in the commercial trade as 'Sensation', reflecting its decidedly distinctive color, which is very dark, together with its size and flowering habit making it a desirable decorative plant.

Spathiphyllum generally are not quite as distinctive as is the instant variety but this cultivar has shown that it retains its distinctive characteristics from generation to generation.

I have caused the cultivar to be asexually reproduced by tissue culture and the characteristics described have been shown to come true.

This cultivar was developed in a program where the seed parent was Spathiphyllum C. 'Fantastica' a cultivar developed in the same program as the instant cultivar but not patented the pollen parent being the Spathiphyllum C. 'Supreme' likewise a product of the same program but not patented either.

The cultivar hereof is compared with some of the prior known cultivar such as C. 'Supreme' and C. 'Lynese' as well as a cultivar identified as C. 'St. Mary', none of which is patented. The instant cultivar has a taller wider habit with fewer suckers than the prior cultivars and a leaf of longer broader form. These distinctions, together with the dark color make the same outstanding along with the more shiny aspect of the leaves.

My new cultivar 'Sensation' produces white flowers, the Spathe being approximately 28 to 31 cm. high and 13 to 15 cm. wide standing slightly above or even with the foliage when grown in a 15 gallon container.

My new plant becomes mature with a size of approximately 1.4 meters to 1.5 meters high and 2 meters to 2.4 meters wide after approximately 70 to 80 weeks under favorable growing conditions from a tissue culture beginning.

More specifically my new cultivar is disclosed in the drawing attached hereto which is in color, the color references being to The Royal Horticultural Society Colour Chart and nomenclature likewise developed therefrom with the plates indicated by number.

The color disclosure is one which is as nearly like that of the actual plant as is possible to obtain in a color reproduction of this kind made by photographic process.

A more detailed description of certain of the important and notable aspects of my new cultivar is set forth in the following, noting that the plant was developed in Hollywood, Fla. and has been grown and reproduced there as well as in Altha, Fla.

The detailed description following assists in identifying the plant and indicating certain of the distinctive characteristics thereof.

Parentage:

*Seed parent.*—C. 'Fantastica'.

*Pollen parent.*—C. 'Supreme'.

Leaves:

*Form.*—Simple elliptic with acute apices and obtuse base; leaf blade entire.

*Size.*—At maturity approximately 60 cm to 76 cm in length and approx. 28 cm to 36 cm in width.

*Veins.*—Well defined; sunken (Rugose).

*Petiole.*—Alate.

*Color.*—Using The Royal Horticultural Society Colour Chart. Immature leaf — Adaxial side: 137A. Abaxial side: 137D. Mature leaf — Adaxial side: 147A. Abaxial side: 138A.

*Height.*—Approx. 1.1 meters to 1.4 meters from soil level.

Inflorescence:

*Type.*—Spathe and Spadix.

*Immature.*—Spathe tightly rolled around Spadix and extrudes form petiole sheath. The Spathe is fully opened approx. when the pedicel is fully elongated approx. 1.4 meters to 1.5 meters from the soil surface.

*Spathe.*—28 cm to 31 cm in height. 13 cm to 15 cm in width.

*Color.*—155A at maturity.

*Arrangement.*—Straight upright; born on pedicle.

*Shape.*—Ovate with acute apices with aristate tendencies; base obtuse; slightly cupped.

Flowering time: After approximately 10 months to 12 months depending on season, approximately 1 to 4 blossoms will be present. Smaller blossoms may occur on less mature plants.

Reproductive organs:

*Spadix.*—Approximately 12 cm to 13 cm high. Approximately 2.0 cm to 2.5 cm diameter.

*Color.*—155A.

*Stamens.*—Anthers and filaments not clearly visible.

*Pistil.*—Protruding between staminate flowers, firmly fixed to main axle.

Roots: White fleshy main roots with fine lateral roots.

I claim:

1. A new and distinct Spathiphyllum cultivar, substantially as herein shown and described, characterized particularly as to novelty by the taller, wider habit than either parent, fewer suckers than several known varieties, longer, broader leaves of darker color and more shiny than either parent, white flowers and particularly attractive aspect for ornamental use.

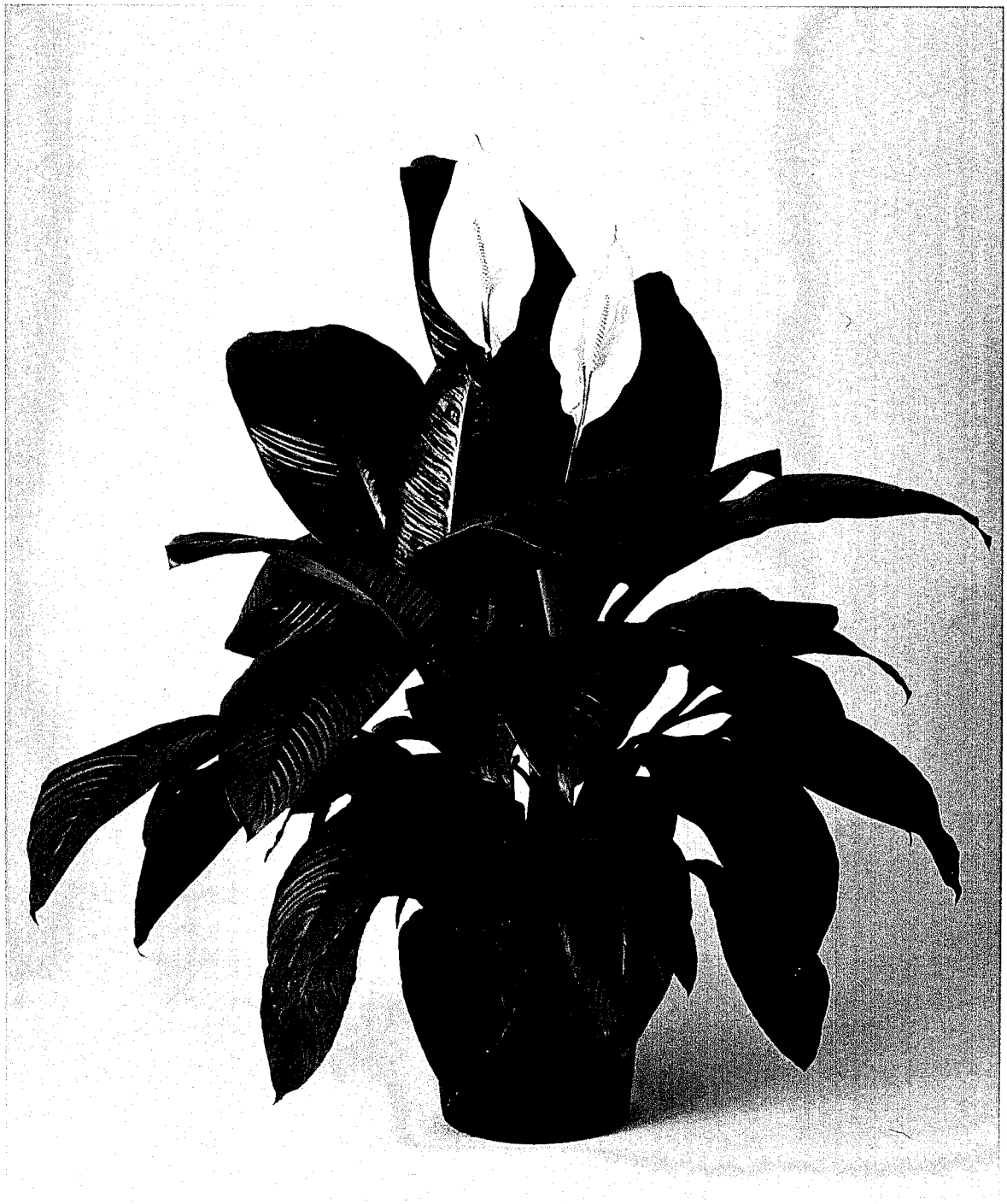

* * * * *